United States Patent [19]
Gaylord, Jr. et al.

[11] Patent Number: 5,343,504
[45] Date of Patent: Aug. 30, 1994

[54] NUCLEAR FUEL BUNDLE SPACER SPRING CONSTANT GAUGE

[75] Inventors: William B. Gaylord, Jr.; Donald F. Butzin; Robert K. Williams, all of Wilmington, N.C.

[73] Assignee: General Electric Company, San Jose, Calif.

[21] Appl. No.: 22,233

[22] Filed: Feb. 25, 1993

[51] Int. Cl.⁵ .................................. G21C 17/00
[52] U.S. Cl. .................................. 376/247; 376/245
[58] Field of Search ............... 376/245, 247, 441; 73/161

[56] References Cited

U.S. PATENT DOCUMENTS

| | | | |
|---|---|---|---|
| 4,028,811 | 6/1977 | Hutter et al. | 33/174 L |
| 4,086,809 | 5/1978 | Wu et al. | 73/161 |
| 4,108,719 | 8/1978 | Olshausen | 376/245 |
| 4,246,783 | 1/1981 | Steven et al. | 73/161 |
| 5,215,705 | 6/1993 | Butzin et al. | 367/247 |
| 5,226,633 | 7/1993 | Willard, Jr. | 267/159 |

*Primary Examiner*—Donald P. Walsh
*Assistant Examiner*—Meena Chelliah
*Attorney, Agent, or Firm*—J. S. Beulick

[57] ABSTRACT

To measure the spring constants of double-acting, fuel rod-centering springs assembled with different pairs of ferrules in a nuclear fuel bundle spacer, a gauge is provided to include an alignment rod and a probe carried by a handle for insertions into the ferrules of a ferrule pair. The alignment rod loads the side of the spring acting in its ferrule, while the other spring side exerts its fuel rod-centering force on a load cell carried by the probe. A micrometer acts against the load cell to produce measured deflections of the other spring side. Spring constants are calculated from electrical readouts of spring force and spring deflection from the load cell and micrometer.

10 Claims, 1 Drawing Sheet

NUCLEAR FUEL BUNDLE SPACER SPRING CONSTANT GAUGE

BACKGROUND OF THE INVENTION

Nuclear power reactors are a well known source of energy. In one type of nuclear reactor the nuclear fuel is comprised of elongated rods formed of sealed cladding tubes of suitable material, such as a zirconium alloy, containing uranium oxide and/or plutonium oxide as the nuclear fuel. A number of these fuel rods are grouped together and contained in an open-ended tubular flow channel to form a separately removable fuel assembly or bundle. A sufficient number of these fuel bundles are arranged in a matrix, approximating a right circular cylinder, to form the nuclear reactor core capable of self-sustaining a fission reaction. The core is submerged in a fluid, such as light water, which serves both as a coolant and as a neutron moderator.

A typical fuel bundle is formed by an array of spaced fuel rods supported between upper and lower tie plates; the rods typically being in excess of ten feet in length, on the order of one-half inch in diameter and spaced from one another by a fraction of an inch. To provide proper coolant flow past the fuel rods it is important to maintain the rods in precisely controlled, spaced relation such as to prevent bowing and vibration during reactor operation. A plurality of fuel rod spacers are thus utilized at spaced intervals along the length of the fuel bundle for this purpose.

Design considerations of such fuel rod bundle spacers include the following: retention of rod-to-rod spacing, retention of fuel bundle shape, allowance for fuel rod thermal expansion, restriction of fuel rod vibration, ease of fuel bundle assembly, minimization of contact areas between spacer and fuel rods, maintenance of structural integrity of the spacer under normal and abnormal (such as seismic) loads, minimization of reactor coolant flow distortion and restriction, maximization of thermal limits, minimization of parasitic neutron absorption, and minimization of manufacturing costs including adaptation to automated production.

Commonly assigned Matzner et al. U.S. Pat. No. 4,508,679 discloses and claims a nuclear fuel rod bundle spacer uniquely constructed to address these design concerns. As disclosed therein, a spacer is formed of an array of conjoined tubular cells or ferrules surrounded by a peripheral support band, each ferrule bore thus providing a passage through which a fuel rod or other elongated element of the fuel bundle is inserted. The ferrules are spot welded together and to the peripheral support band to provide an assembly of high structural strength.

The rods or elements extending through the ferrules are centered and laterally supported therein between rigid projections or stops and resilient members. The rigid projections or stops are inwardly formed as fluted or dimpled portions of the ferrule wall at locations near the upper and lower ferrule edges to maximize the axial distance therebetween and thus enhance fuel rod support.

The resilient members take the form of slender continuous loop springs of generally elliptical shape held captive by oppositely directed tabs formed by C-shaped cutouts in the walls of a pair of adjacent ferrules, whereby the two sides of each spring member project into the bores of its ferrule pair. Thus, a single spring serves two ferrules in biasing the fuel rods into contact with the two axially spaced pairs of stops pursuant to centering the rods in the ferrule bores.

In commonly assigned U.S. Patent Application entitled "Nuclear Fuel Bundle Spacer Spring Force Gauge", Ser. No. 07/659,664, filed Feb. 25, 1991, a gauge is disclosed for measuring the fuel rod-centering forces exerted by the two sides of the Matzner et al. double-acting springs assembled in a manufactured spacer as a quality assurance check prior to being put into nuclear reactor service. It is also desirable to determine the integrity of these springs at times of reactor servicing and/or refueling. It has been determined that the most reliable integrity check to determine whether long periods of high temperature and radiation exposure have degraded the utility of these springs is to measure their spring constant (ratio of spring force to spring deflection).

SUMMARY OF THE INVENTION

It is accordingly an objective of the present invention to provide a gauge suitable for quality assurance application to measure the spring constant of double-acting, fuel rod-centering springs assembled in spacers employed in nuclear fuel bundles.

Additional objectives and advantages of the invention will be set forth in part in the description which follows, and in part will be obvious from the description, or may be learned by practice of the invention. The objectives and advantages of the invention will be realized and attained by means of the elements and combinations particularly pointed out in the appended claims.

To achieve the objectives and in accordance with the purpose of the invention, as embodied and described herein, the invention comprises a gauge for measuring the spring constants of double-acting springs assembled with different pairs of ferrules in a spacer of a nuclear fuel bundle, wherein each spring has a first resilient side acting in one ferrule of each ferrule pair to exert a fuel rod centering force and a second resilient side acting in the other ferrule of each pair to exert a separate fuel rod centering force. The spring constant gauge includes an alignment rod for insertion into one of the ferrules of a pair to simulate the presence of a fuel rod and thus load the first resilient side of the spring. The gauge also includes a probe for insertion into the other ferrule of the ferrule pair also to simulate the presence of a fuel rod.

A force measuring device is included with the probe and is subjected to the fuel rod-centering force exerted by the second resilient side of the spring. A deflection measuring device is also provided to induce plural measured deflections of the second resilient side of the spring. The spring force readouts of the force measuring device and the spring deflection readouts of the deflection measuring device are fed to a spring constant indicating device.

It is to be understood that both the foregoing general description and the following detailed description are exemplary and explanatory only and are not restrictive of the invention as defined in the appended claims.

The accompanying drawing, which is incorporated in and constitutes a part of this specification, illustrates an embodiment of the invention and together with the description, serves to explain the principles of the invention.

BRIEF DESCRIPTION OF THE DRAWINGS

Corresponding reference numerals refer to like parts throughout the several views of the drawing.

DETAILED DESCRIPTION

Figures 1, 2:
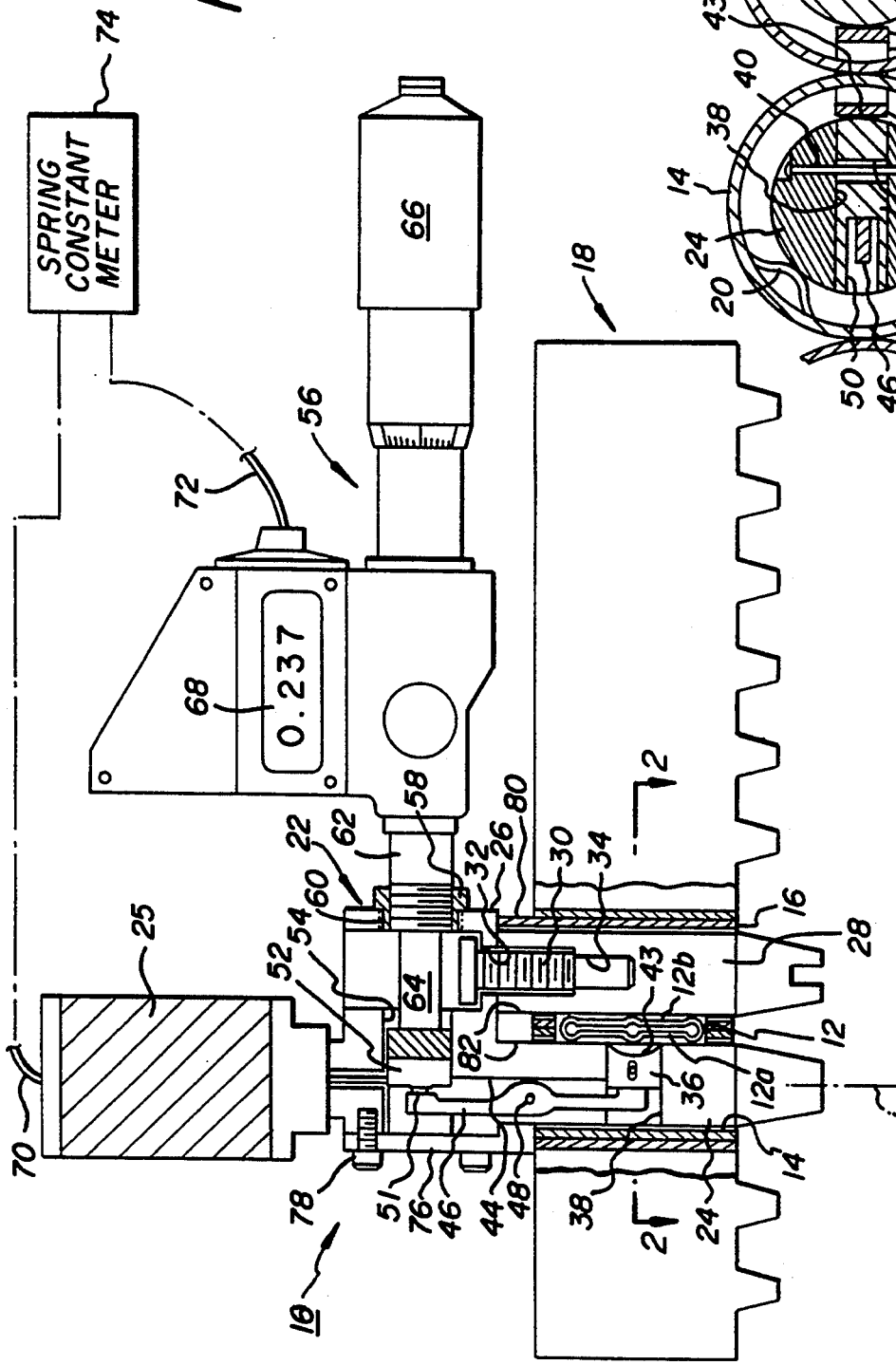
FIG. 1 is an elevational view, partially in section, of a nuclear fuel bundle spacer spring constant gauge constructed in accordance with an embodiment of the present invention.
FIG. 2 is an enlarged sectional view taken along line 2—2 of FIG. 1.

The spring constant gauge of the present invention, generally indicated at 10 in FIG. 1, is illustrated in position to measure the spring constant of a spring 12 assembled with a pair of ferrules 14 and 16 of a nuclear fuel bundle spacer, generally indicated at 18. For details of the spacer construction, reference may be had to the above-cited Matzner et al. patent, the disclosure of which is expressly incorporated herein by reference. As mentioned above in connection with this patent, spring 12 is a double-acting loop spring of generally elliptical shape having one resilient side 12a acting in ferrule 14 and a second resilient side 12b acting in ferrule 16. Thus, spring side 12a exerts a force on a fuel rod (not shown) inserted through ferrule 14 to bias it against inwardly formed stops 20, best seen in FIG. 2, thereby maintaining the fuel rod centered within the ferrule bore. Spring side 12b performs the same function with respect to a fuel rod inserted through ferrule 16. Gauge 10 is uniquely structured to accurately measure the spring constant of the individual spring sides 12a, 12b to determine if spring 12 meets quality assurance standards.

Thus, as seen in FIGS. 1 and 2, gauge 10 includes a gauge body, generally indicated at 22, having a depending cylindrical probe 24 for insertion into a ferrule, ferrule 14 in the drawing. The upper end of the gauge body is joined with a handle 25 to accommodate manual or robotic manipulation of the gauge into spring constant gauging position. An integral flange 26, extending laterally from the gauge body, serves to mount a cylindrical alignment rod 28 via a shouldered bolt 30 extending through a clearance hole 32 in the flange and threaded into a counter-sunk and tapped axial bore 34 in the alignment rod. Thus, as probe 22 is inserted into ferrule 14, alignment rod 28 is inserted into ferrule 16.

The diameters of the alignment rod and the probe are each equal to the nominal diameter of a fuel rod, and thus their insertions into the ferrule bores simulate the presence of fuel rods. The shoulder of bolt 30 bottoms out on the shoulder of bore 34 before the bolt head can clamp down on flange 26 to provide for limited floating motion of the alignment rod relative to the probe body. This feature accommodates acceptably minor nonparallelism between the axes of the alignment rod and the probe as spring 12 forces them against stops 20 and into centered portions in their respective ferrule bores.

A plunger 36 is received in a bore 38 formed in the probe, which is oriented transversely to probe axis 39. The plunger is loosely captured in this bore by a roll pin 40 passing through a transversely elongated hole 42 in the plunger. Thus the plunger is free for limited reciprocation in its bore. The axial location of the plunger is such that its face 43, which is of a curvature corresponding to that of a fuel rod peripheral surface, confronts and is acted upon by side 12a of the spring, while spring side 12b is being loaded by the presence of the alignment rod in ferrule 16. The plunger is then subjected to the fuel rod-centering force exerted by spring side 12a in ferrule 14.

The gauge body 22, including probe 24, is formed with an axially elongated slot 44 opening at its lower end into transverse bore 38 for accommodating an elongated arm 46 pivotally mounted to the gauge body at a mid-length point by a roll pin 48. The lower end of the arm extends into a slot 50 formed in the plunger to present a contact surface in engagement with the plunger at the bottom surface of the slot. The upper end of the arm is positioned to engage the tip 51 of a miniature load cell 52 slidingly received in a transverse bore 54 formed in the gauge body. The load cell may be of a conventional button strain gauge type, such as an Omega model LCK-25 available from Omega Engineering of Stamford, Conn.

A micrometer, generally indicated at 56, is mounted to gauge body 22 by means of a bushing 58 having external threads engaging a tapped hole 60 in the gauge body and internal threads engaging a threaded collar 62 of the micrometer. The spindle 64 of the micrometer extends coaxially with bore 54 into abutting engagement with the back end of load cell 52. Rotation of the micrometer thimble 66 adjusts the extension of spindle 64 in convention fashion, which is seen to be effective in linearly varying the position of the load cell in bore 54. By virtue of the mechanical coupling provided by pivotal arm 46, variation of the linear position of the load cell in its bore 54 correspondingly varies the linear position of plunger 36 in its bore 38, resulting in deflection variation of side 12a of spring 12. The micrometer can be easily calibrated to a zero deflection reading by varying the extension position of spindle 64 until the output of load cell 52 is reduced to a zero spring force reading. Then thimble 66 is rotated to produce a measured deflection of side 12a of spring 12 and a spring force reading is taken from the load cell. Preferably spring force readings are taken at several spring deflection values and analyzed to determine an appropriate spring constant value i.e., the ratio of spring force or load to spring deflection, for each of the sides 12a, 12b of the springs.

As seen in FIG. 1, spring deflection readings may be taken from a micrometer display 68. Preferably however, particularly in the case of spring constant gauging in a "hot cell", spring force measurements by the load cell and spring deflection measurements by the micrometer are read out over leads 70 and 72, respectively, to a remote spring constant indicating meter 74. Moving gauge 10 between gauging positions and rotation of the micrometer thimble are effected by manually controlled manipulators or automatically controlled "pick and place" robotic apparatus. A micrometer particularly suited for application in the present invention is a Series 350-712 digimatic micrometer head available from Mitutoyo of Paramus, N.J.

It will be appreciated that, rather than a simple spring constant meter, the load cell and micrometer readouts may be fed to a data acquisition system where they are processed and recorded for subsequent printout of the spring constants of the individual springs identified by their locations in spacer 18.

Completing the description of the gauge construction, an L-shaped spacer cover includes a vertical portion 76 affixed to gauge body 22 by screws 78 and a lateral portion 80 having holes 82 through which alignment rod 28 and probe 24 extend. The lateral portion serves a spacing function by engaging the upper edges of the ferrules to control the depth of alignment rod-probe insertion and thus ensure that the plunger face is properly aligned with the spring side whose spring constant is to be measured.

The present invention thus provides a compact gauge which is conveniently inserted into the multiple ferrules of a nuclear fuel bundle spacer in succession to accurately measure the spring constants of the multiplicity of springs in the spacer. This quality assurance test can be performed expeditiously to qualify spacers for service in a reactor.

Other embodiments of the invention will be apparent to those skilled in the art from consideration of the specification and practice of the invention disclosed herein. It is intended that the specification be considered as exemplary only with the true scope and spirit of the invention being indicated by the following claims.

We claim:

1. A gauge for measuring the spring constants of double-acting springs assembled with different pairs of ferrules in a spacer of a nuclear fuel bundle, wherein each spring has a first resilient side acting in a first ferrule of each pair to exert a fuel rod centering force and a second resilient side acting in a second ferrule of each pair to exert a separate fuel rod centering force, said gauge comprising, in combination:

an alignment rod for insertion into the first ferrule of a selected pair of ferrules to simulate the presence of a fuel rod and thus load the first resilient side of a spring assembled with the selected pair of ferrules;

a probe for insertion into the second ferrule of the selected pair of ferrules to simulate the presence of a fuel rod;

a force measuring device included in said probe in mechanically coupled relation with the second resilient side of the spring to indicate a magnitude of the centering force exerted by the second resilient side of the spring in the second ferrule;

a deflection measuring device mechanically coupled with the second resilient side of the spring and operable to produce plural measured deflections of the second resilient side of the spring; and means connected and responsive to said force measuring device and said deflection measuring device for indicating a spring constant of the second resilient side of the spring.

2. The gauge defined in claim 1, wherein said force measuring device is a load cell.

3. The gauge defined in claim 1, wherein said deflection measuring device is a micrometer.

4. The gauge defined in claim 2, wherein the load cell develops first electrical signals indicative of the centering force of the second resilient side of the spring, and wherein the deflection measuring device develops second electrical signals indicative of the deflections produced on the second resilient side of the spring, the spring constant indicating means connected to receive the first and second signals.

5. The gauge defined in claim 4, wherein said deflection measuring device is a micrometer.

6. The gauge defined in claim 5, wherein the load cell is mounted for incremental linear motion by the probe, and the micrometer includes a spindle engaging the load cell to produce linear motion of the load cell and measured deflections of the second resilient side of the spring.

7. The gauge defined in claim 6, wherein the probe includes an axis oriented substantially parallel with an axis of the second ferrule upon insertion of the probe therein, and a plunger mounted by the probe for movement transversely of the probe axis and having a face simulating a peripheral surface portion of a fuel rod, the plunger face disposed in engagement with the second resilient side of the spring.

8. The gauge defined in claim 7, wherein the probe further includes an elongated arm having first and second ends, the arm being pivotally mounted intermediate the first and second ends to the probe, the first end of the arm engaging the plunger and the second end of the arm engaging a first end of the load cell, the micrometer spindle engaging a second end of the load cell opposite the first end.

9. The gauge defined in claim 8, wherein the load cell is slidingly received in a bore of the probe oriented transversely to the body axis.

10. The gauge defined in claim 9, which further includes means commonly mounting the alignment rod, the probe and the micrometer.

* * * * *